United States Patent [19]

Segev

[11] Patent Number: 5,437,977
[45] Date of Patent: Aug. 1, 1995

[54] DNA PROBE SIGNAL AMPLIFICATION

[75] Inventor: David Segev, 1125 52nd St., Brooklyn, N.Y. 11219

[73] Assignee: David Segev, Mazkeret Batya, Israel

[21] Appl. No.: 908,584

[22] Filed: May 29, 1992

Related U.S. Application Data

[63] Continuation of Ser. No. 503,621, Apr. 3, 1990, abandoned.

[51] Int. Cl.$^6$ ............................................. C12Q 1/68
[52] U.S. Cl. ........................................ 435/6; 935/77; 935/78
[58] Field of Search ...................... 435/6; 436/501, 94; 935/77, 78; 536/27

[56] References Cited

U.S. PATENT DOCUMENTS

| | | | |
|---|---|---|---|
| 4,302,204 | 11/1981 | Wahl et al. | 435/6 |
| 4,683,195 | 7/1987 | Mulws et al. | 435/6 |
| 4,716,106 | 12/1987 | Chiswell et al. | 435/6 |
| 4,724,202 | 2/1988 | Dattagupta et al. | 435/6 |
| 4,731,325 | 3/1988 | Palva et al. | 435/6 |
| 4,762,780 | 8/1988 | Spector et al. | 435/6 |
| 4,868,105 | 9/1989 | Urdea et al. | 435/6 |
| 4,882,669 | 11/1989 | Schneider et al. | 435/6 |

FOREIGN PATENT DOCUMENTS

| | | | |
|---|---|---|---|
| 0204510 | 12/1986 | European Pat. Off. | 435/6 |
| 0245206 | 11/1987 | European Pat. Off. | 436/501 |
| 0292128 | 11/1988 | European Pat. Off. | 536/27 |
| 317077 | 5/1989 | European Pat. Off. | 435/6 |
| 3420925 | 12/1985 | Germany | 436/6 |

OTHER PUBLICATIONS

Horn et al., Nucleic Acids Research 17, 6959–6967 (1989).
Teng et al., Nucleic Acids Research 16, 2671–2690.

*Primary Examiner*—Stephanie W. Zitomer
*Attorney, Agent, or Firm*—Irving N. Feit; Eric J. Sheets

[57] ABSTRACT

A method for amplifying a signal during the detection of target nucleic acid molecules utilizes a primary oligonucleotide probe that binds to a bridging nucleic acid molecule. The bridging molecule hybridizes to a first developer nucleic acid molecule. Each first developer molecule comprises: (a) a first branch having a sequence of at least two different nucleotides and at least six total nucleotides complementary to a sequence of a first branch of a second developer molecule; (b) a second branch comprising a sequence of at least two different nucleotides and at least six total nucleotides complementary to a sequence of a second branch of the second developer molecule; and (c) a detectable label. In the method, the bridging molecule binds to the primary probe and hybridizes to the first developer molecule; the bound first developer molecule hybridizes to the second developer molecule to form a developer chain; additional first and second developer molecules are added to the chain; and the labeled developer molecules in the developer chain are detected.

7 Claims, 2 Drawing Sheets

DNA PROBE SIGNAL AMPLIFICATION

This application is a continuation of Ser. No. 07/503,621 filed Apr. 3, 1990, now abandoned, and is incorporated herein by reference.

DNA probes are important tools in cell and molecular biology. Specific genes have been located in cDNA and genomic libraries, and have been localized to individual chromosomes through the use of such probes. In addition, labelled DNA probes have been used to detect pathogens such as viruses and bacteria in biological fluids and tissue samples.

A labelled DNA probe is typically an oligonucleotide conjugated to a label, such as a reporter molecule. The oligonucleotide may be synthetic or natural, and is complementary to a portion of the sequence of the target DNA molecule. The reporter molecule may be radioactive or non-radioactive. Non-radioactive reporter molecules are generally preferred for safety and environmental reasons. Some common non-radioactive reporter molecules are detectable enzymes, fluorescent molecules, and biotin. The probe may be attached to the label directly. Alternatively, the probe may be conjugated to a ligand and detected with a label that is bound to a receptor of the ligand. For example, the probe may be conjugated to biotin and detected through the use of avidin or streptavidin that is labelled with a reporter group or of a labelled antibody against biotin.

In order to detect very low levels of target DNA molecules, it is often necessary to increase the sensitivity of the assay. The sensitivity may be increased in two ways—target amplification and signal amplification.

Target amplification may be carried out by the so-called polymerase chain reaction (PCR) method of Cetus Corporation as described in U.S. Pat. No. 4,683,195. This method is based on the use of two oligonucleotides to prime DNA synthesis catalyzed by a polymerase. The two primers are complementary to sequences of opposite strands of double-stranded DNA. DNA synthesis occurs in each strand across a region spanned by the priming sites of the target DNA being amplified. By repeated cycles of denaturing the DNA strands, annealing nucleotide primers and initiating DNA synthesis with polymerase, an exponential increase of the target DNA is achieved. This method has been reviewed by Gyllensten in *Biotechniques* 7, 700–706 (1989).

Although PCR is effective in some cases, problems—such as excessive noise and false positives—exist. The deficiencies of the PCR method are discussed in the Gyllensten review.

A different approach to increasing sensitivity of nucleic acid assays using oligonucleotide probes is to amplify the signal. For example, Segev, European Patent Application 292,128, discloses oligonucleotide probes with increased sensitivity. Each probe has multiple branches for labelling.

Chiswell, U.S. Pat. No. 4,716,106, discloses assays using a primary oligonucleotide probe and a complementary secondary probe to which is attached multiple labelling groups. Schneider and Shenk, U.S. Pat. No. 4,882,269, discloses hybridization assays wherein a sequence of a primary probe hybridizes to the target nucleic acid molecule and a plurality of labelled secondary probes hybridize to different sequences of the primary probe. The primary and secondary probes covered by U.S. Pat. No. 4,882,269 constitute the AmpliProbe TM System of ImClone Systems Incorporated. Palva et al, U.S. Pat. No. 4,731,325, discloses hybridization assays wherein more than one probe binds to the target nucleic acid molecule.

In Urdea et al, U.S. Pat. No. 4,868,105, hybridization assays are disclosed wherein multiple primary probes bind to a target nucleic acid molecule. Labelled secondary probes hybridize to the primary probes.

The need for even greater signal amplification has led to suggestions and speculation that chains of labelled secondary oligonucleotide probes bound to a primary probe would lead to highly sensitive hybridization assays. For example, Urdea, European Patent Application 317,077, discloses hybridization assays for target nucleic acid molecules. One or more primary probes, called amplifier probes, hybridize to the target molecule. A secondary probe, called a multimer, hybridizes to the primary probe or probes. The secondary probe may be linear or branched. Sequences of the secondary probe hybridize to a multiplicity of labelled oligonucleotides. Urdea et al speculate that the secondary probes may also be bound to each other in a series. There is, however, no disclosure of how such a series of secondary probes may be formed. The series of secondary probes proposed by Urdea et al is impractical, since a number of oligonucleotides equal to the number of secondary probes in the series would have to be prepared.

Similarly, Collins, European Patent Application 204,510, discloses hybridization assays involving the use of a primary probe, called a receptor probe, a secondary probe, called an amplifier strand, and a labelled strand capable of hybridizing to the amplifier strand. The receptor probe hybridizes to the target nucleic acid molecule, and has a homopolymeric nucleotide tail. The amplifier strand contains a homopolymeric nucleotide strand capable of hybridizing to the tail of the receptor probe. The labelled strand contains a homopolymeric nucleotide strand capable of hybridizing to the amplifier strand. Collins further speculates that a second homopolymeric amplifier strand may be hybridized to the preceding amplifier strand, and a second labelled strand may be hybridized to the amplifier strand. This further step may be repeated to build a network of amplifier strands and label strands.

The homopolymeric nucleotide probes disclosed by Collins are deficient in that one has no control over the extent to which each such probe hybridizes to its complementary partner. For example, the second amplifier probe may hybridize so extensively with the first amplifier probe that there is an insufficient number of remaining single-stranded nucleotides to hybridize with a third amplifier strand. In addition, one is not able to maximize the stability of the series of amplifier strands by maximizing the hybridization of each amplifier strand to two additional amplifier strands.

A need continues to exist for hybridization assays wherein a primary probe hybridizes to a series of secondary probes wherein the above-mentioned deficiencies are corrected. One objective of the present invention is to provide such hybridization assays. Further objectives of the present invention are to provide hybridization assays having less noise, greater sensitivity, and higher signal/noise ratios, and greater speed than has been achievable with previously known methods. An additional objective is to provide for exponential signal amplification in DNA hybridization assays.

SUMMARY OF THE INVENTION

These and other objectives as will be apparent to those with ordinary skill in the art have been achieved by providing a method for amplifying a signal during the detection of target nucleic acid molecules comprising the steps of:

a) hybridizing a first sequence of a primary oligonucleotide probe to the target nucleic acid molecules wherein the primary probe has a means for binding to a bridging nucleic acid molecule, the bridging molecule being capable of hybridizing to at least one developer nucleic acid molecule;

b) exposing the primary probe to the bridging molecule and to a first developer molecule and a second developer molecule, each developer molecule comprising:
   i) a first branch comprising a sequence of at least two different nucleotides and at least six total nucleotides complementary to a sequence of a first branch of the other developer molecule;
   ii) a second branch comprising a sequence of at least two different nucleotides and at least six total nucleotides complementary to a sequence of a second branch of the other developer molecule; and
   iii) a detectable label or a means of being converted into a developer molecule comprising a detectable label;

wherein the first developer molecule and the second developer molecule have structures that are the same or different; and steps a and b being conducted under conditions such that:
   i) the bridging molecule binds to the primary probe and hybridizes to the first developer molecule; and
   ii) the bound first developer molecule hybridizes to the second developer molecule to form a developer chain; and c) detecting the labeled developer molecule in the developer chain.

In a particularly efficient embodiment, the present invention provides a method for amplifying a signal during the detection of target nucleic acid molecules comprising the steps of:

a) hybridizing a first sequence of a primary oligonucleotide probe to the nucleic acid target molecules wherein the probe has a means for binding to a bridging molecule, the bridging molecule being capable of hybridizing to at least one self-complementary developer molecule;

b) exposing the probe to the bridging molecule and to a plurality of developer molecules having at least three branches, each branch of the developer molecule having a sequence of at least six nucleotides that is complementary to a sequence of at least one other branch of the same or of another developer molecule; each developer molecule:
   i) being capable of hybridizing to at least three other developer molecules; and
   ii) containing, or being capable of containing, a detectable label;

under conditions such that:
   i) the bridging molecule binds to the primary probe and hybridizes to at least one developer molecule;
   ii) at least two additional developer molecules hybridize to the first developer molecule; and
   iii) a plurality of other developer molecules hybridize to the hybridized additional developer molecule to form a developer chain; and c) detecting the labelled developer molecules in the developer chain.

The present invention further provides a method for detection in DNA hybridization assays. The method comprises a method for detecting the presence of a nucleic acid sequence comprising the steps of:

a) contacting the nucleic acid with a molecule that:
   i) is not a complementary nucleic acid sequence; and
   ii) binds specifically to the nucleic acid sequence; and b) detecting the presence of the bound molecule.

FIGURES

Certain embodiments of the invention may be seen from the Figures.

In the embodiment of FIG. 3, all the nucleotides of each developer molecule hybridize to the bridging molecule and at least one other developer molecule, or to at least two other developer molecules in the developer chain, except for the last developer molecule. In this embodiment, there is no gap between the developer molecules in the chain. The developer molecules may be ligated to form a concatamer 60.

In the embodiment shown in FIG. 4, the developer molecules are branched (70). Each branched developer molecule is capable of hybridizing to at least three other developer molecules, or to at least two other developer molecule and the bridging molecule.

DETAILED DESCRIPTION OF THE INVENTION

The Target Nucleic Acid Molecule

The target nucleic acid molecules that can be detected in accordance with the present invention may be any nucleic acid molecule. The nucleic acid molecule may be DNA or RNA having any sequence of adenine (A), thymine (T), cytosine (C), and guanine (G), or, in the case of RNA, uracil (U). The nucleic acid may be single-stranded or double-stranded. There is no maximum limit to the length of the target nucleic acid molecule. The molecule should have at least six nucleotide bases.

The hybridization assays possible with the present invention may be conducted in solution, although it is preferable for the target nucleic acid molecule to be fixed to a solid surface. Immobilization of the target nucleic acid molecule facilitates detection by permitting separation of the nucleic acid molecule from non-immobilized components by a simple washing step. The immobilization of the target nucleic acid molecule may occur during any stage of the assay prior to detection. Any solid surface capable of fixing the target nucleic acid molecule may be used in the present invention. Some suitable solid supports include nitrocellulose, agarose beads, modified cellulose fibers, polypropylene, and the like. The solid surface may conveniently be the wall of the vessel in which the assay occurs.

The target nucleic acid sequence is bound to the solid support by methods known in the art. Such methods include covalent bonding and non-covalent bonding.

Examples of non-covalent bonding include hybridization of a nucleotide sequence of the target molecule complementary to that of a nucleotide sequence immobilized on the solid surface. Such immobilized sequences are often referred to as capture probes.

Alternatively, the target nucleic acid molecule may contain a ligand that binds specifically to a receptor on the solid surface. Any ligand-receptor combination that does not interfere with the hybridization of the target nucleic acid molecule to the primary probe is suitable. Some examples include, for example, biotin-avidin, thyroxine-thyroxine-binding globulin, carbohydrate-lectin, antibody-antigen and the like. Either member of such combinations may constitute the ligand or the receptor.

The Primary Probe

The primary probe is a branched or unbranched nucleic acid molecule having a first sequence of nucleotides capable of hybridizing to a sequence of the target molecule. The hybridization occurs under normal hybridizing conditions, such as, for example, temperatures between 15-60 degrees centigrade; pH between 6-. Preferably, the primary probe has a sequence that is complementary to at least six nucleotides of the target molecule.

Figure 1:
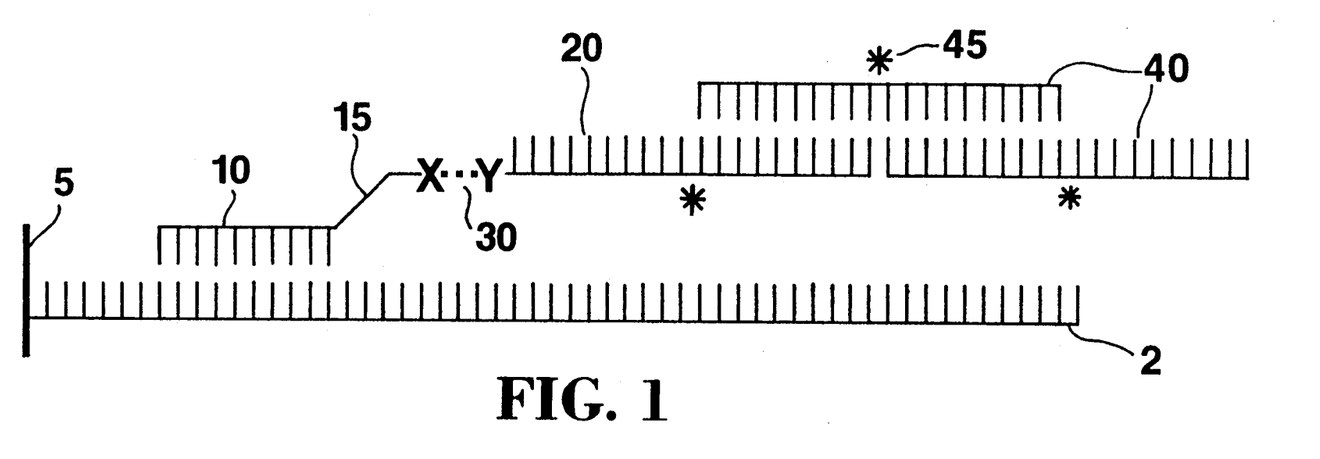
In FIG. 1, a target polynucleotide molecule (2) is immobilized on solid surface (5). First sequence (10) of primary probe (15) hybridizes specifically to a sequence of target molecule (2). Primary probe (15) binds to bridging molecule (20) through means (30). Developer molecule (40) hybridizes to the bridging molecule (20) and to additional developer molecules (40). The developer molecules are detectable through label (45).
Figure 2:
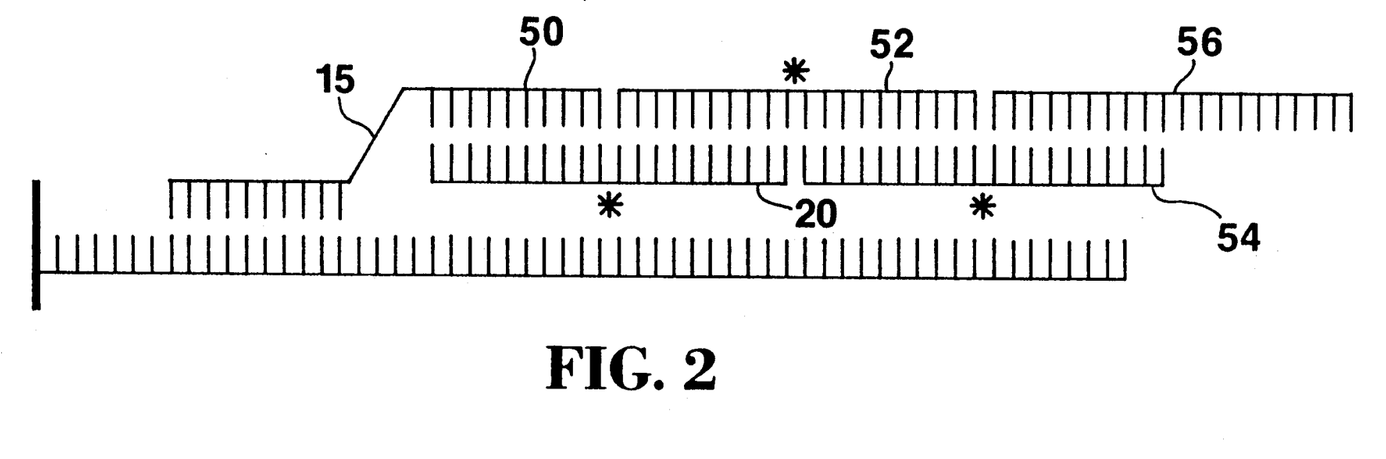
FIG. 2 is similar to FIG. 1, except that the means for binding primary probe (15) to bridging molecule (20) is a second sequence of the primary probe (50) that hybridizes to a sequence of the bridging molecule (20).

The primary probe also has a means for binding a bridging molecule. The means for binding the primary probe to the bridging molecule, as shown in FIG. 2, which is referred to as X-Y (30) in FIG. 1, may be any of the ligand-receptor relationships mentioned above. Preferably, however, the primary probe (15) binds to the bridging molecule (20) by means of a second sequence (50) of the primary probe that is complementary to at least six contiguous nucleotides of the bridging molecule. The complementary sequences of the primary probe and of the bridging molecule are selected so that the target molecule does not interfere with the hybridization of the primary probe to the bridging molecule.

The length of the primary probe is not critical, as long as it stably hybridizes to the target molecule and binds to the bridging molecule under normal hybridization conditions. Preferably, the primary probe is not longer than necessary. For example, a linear primary probe is preferably an oligonucleotide having 12-100 nucleotide bases. The upper limit of nucleotides is not critical, but is determined by convenience, such as a shorter hybridization time.

The Bridging Molecule

The bridging molecule is a linear or branched nucleic acid molecule that binds to the primary probe and to at least one developer molecule. The binding of the bridging molecule to the primary probe occurs by means (30) of FIG. 1. Preferably, the bridging molecule has a sequence that hybridizes to the second sequence (50) of the primary probe as shown in FIG. 2.

The bridging molecule hybridizes to the developer molecules under approximately the same conditions that the primary probe hybridizes to the target molecule. These conditions have been discussed above.

Preferably, the bridging molecule has a sequence of nucleotides complementary to at least six contiguous nucleotides of the developer molecule. The length of the bridging molecule is not critical, as long as it binds to the primary probe and hybridizes to at least one developer molecule under normal nucleic acid hybridization conditions. For example, a linear bridging molecule is preferably an oligonucleotide having 12-100 nucleotides bases. The bridging molecule may be linear or branched.

The Developer Molecule

The developer molecule is linear or branched and may be self-complementary. For the purpose of this specification, the term "self-complementary" means that each developer molecule is capable of hybridizing to all other developer molecules under normal nucleic acid hybridizing conditions, such as the conditions discussed above.

Each developer molecule is made up of branches, each of which comprises a nucleotide sequence that is complementary to that of other developer molecules. A linear developer molecule is considered to have two branches. A branched developer molecule has more than two branches.

Each developer molecule is capable of hybridizing to at least two other developer molecules or to the bridging molecule and at least one other developer molecule through complementary sequences. The complementary sequences of each developer molecule comprise at least six contiguous nucleotide bases. Preferably, the same sequence that binds a developer molecule to other developer molecules also binds the developer molecule to the bridging molecule.

Chains of developer molecules form under hybridizing conditions. Since each developer molecule is labelled, the extent of amplification resulting from the presently described method increases as the number of developer molecules in the chain increases. There is no limit to the number of developer molecules in the chain. There may be 100 developer molecules, 1,000 developer molecules, 10,000 developer molecules, and even more.

In each chain of developer molecules, each developer molecule hybridizes to at least two other developer molecules. The last molecule in a chain of developer molecules hybridizes only to the previous developer molecule.

Labelling the Developer Molecules

The developer molecule is labelled in accordance with methods known in the art. Such methods have been described, for example, by Leary et al, *Proc. Natl. Acad. Sci.* USA (1983) 80:4045; Renz and Kurz, *Nucl. Acids Res.* (1984) 12:3435; Richardson and Gumport, *Nucl. Acids Res.* (1983) 11:6167; Smith et al, *Nucl. Acids Res.* (1985) 13:2399; Meinkoth and Wahl, *Anal. Biochem.* (1984) 138:267.

The label may be radioactive. Some examples of useful radioactive labels include $^{32}P$, $^{125}I$, $^{131}I$, and $^{3}H$. Use of radioactive labels have been described in U.K. 2,034,323, U.S. Pat. No. 4,358,535, and U.S. Pat. No. 4,302,204.

Some examples of non-radioactive labels include enzymes, chromophors, atoms and molecules detectable by electron microscopy, and metal ions detectable by their magnetic properties.

Some useful enzymatic labels include enzymes that cause a detectable change in a substrate. Some useful enzymes and their substrates include, for example, horseradish peroxidase (pyrogallol and o-phenylenediamine), beta-galactosidase (fluorescein beta-D-galactopyranoside), and alkaline phosphatase (5-bromo-4-chloro-3-indolyl phosphate/nitro blue tetrazolium). The use of enzymatic labels have been described in U.K. 2,019,404, EP 63,879, and by Rotman, *Proc. Natl. Acad. Sci.*, 47, 1981–1991 (1961).

Useful chromofores include, for example, fluorescent, chemiluminescent, and bioluminescent molecules, as well as dyes. Some specific chromofores useful in the present invention include, for example, fluorescein, rhodamine, Texas red, phycoerythrin, umbelliferone, luminol.

The labels may be conjugated to the developer molecule by methods that are well known in the art. The labels may be directly attached to the developer molecules through a functional group on the developer molecule. The developer molecule either contains or can be caused to contain such a functional group. Some examples of suitable functional groups include, for example, amino, carboxyl, sulfhydryl, maleimide, isocyanate, isothiocyanate.

The label may also be conjugated to the developer molecules by means of a ligand attached to the developer molecule by a method described above and a receptor for that ligand attached to the label. Any of the ligand-receptor combinations described above is suitable. The biotin-avidin combination is preferred.

A method for labelling the developer molecules in a way that avoids the requirement for immobilizing the target nucleic acid molecule to a solid support and removing non-immobilized components involves the use of two molecules that can be detected when brought within a certain distance of each other. Such labels will be detectable if, for example, non-radiative energy transfer occurs between them. If the energy absorbed from one of the labels by the other is re-emitted at a different wavelength, the labels can be detected. Such absorption and re-emission occurs when the two labels are within a specific proximity to each other. For example, approximately 10%–90%, preferably approximately 25%–75%, and more preferably approximately 40%–60% of the developer molecules are conjugated to a chemiluminescent catalyst. The remainder of the developer molecules are conjugated to an absorber/emitter moiety. The developer molecules containing the chemiluminescent catalyst and the developer molecules containing the absorber/emitted moiety hybridize to each other so that the chemiluminescent catalyst and the absorber/emitter moiety are sufficiently close in proximity to permit non-radiative energy transfer. The distance between the chemiluminescent catalyst and the absorber/emitter moiety is generally within approximately 100 angstroms or less of each other. In the presence of agents effective for inducing light emission from the chemiluminescent catalyst, a measurable amount of light will be absorbed by the absorber/emitter moiety at a wavelength that can be detected. The absorber/emitter moiety may be a phosphorescent or fluorescent agent. Some examples of suitable chemiluminescent catalysts include peroxidase and luciferase, both of which catalyze the luminol oxidation. Suitable absorber/emitter moieties for the luminol chemiluminescent reaction include free base porphyrins such as uroporphyrin and tetracarboxyphenylporphyrin, metalloporphyrins containing such metals as magnesium or zinc, tetraphenylcarboxyporphyrins, perylene, anthracene, 7-methyldibenzo(a,h)pyrene, and other polycyclic aromatics having conjugated ring systems of sufficient size to produce strong absorbance in the region of luminol chemiluminescence (between 400 and 450 nm). The use of energy transfer labelling of this type is disclosed in European Patent Application 70,685. Related methods are disclosed in U.S. Pat. No. 4,868,103 and 4,822,733.

The present invention further provides a method for labelling DNA probes that has not previously been described. The method is based on the existence of molecules that recognize specific DNA sequences even though the molecules do not contain complementary DNA sequences. The binding may occur by any means other than the hybridization of a complementary DNA sequence, for example by intercalation.

For example, the well known drugs distamycin A and netropsin, and the dye Hoechst 33258, bind selectively to double-stranded DNA that is A-T rich. Preferably, the A-T region comprises AATT, ATTT, or AAATTT. Similarly, the known drugs actinomycin D and chromomycin bind specifically to double-stranded DNA that is G-C rich. The binding of these drugs to DNA has been described by Scott et al, *Biochemistry* 27, 7940–7951 (1988) and Gao et al, *Biochemistry* 28, 751–762 (1989). Hoechst 33258 is described by Teng et al, *Nucl. Acids Res.* 16, 2671–2690 (1988). DNA site-specific peptides and proteins are also known and may be used in the present invention.

In accordance with the present method, site-specific DNA binding compounds are attached to the developer molecules by methods described above. These compounds are detected on the basis of differences in properties of the bound compounds relative to unbound compounds. Such differences include, for example, spectral differences such as UV, NMR, circular dichroism, and others.

The developer molecules may be multiply labelled. Methods for attaching multiple labels to nucleic acid molecules such as those used as developer molecules herein are known in the art. For example, multiple labelling may be achieved by means of branched linker molecules as described by Segev in EP 292,128. The description and examples of branched linker molecules described by Segev in EP 292,128 is incorporated herein by reference.

Structure of Probes

The present invention utilizes three types of probes. A primary probe hybridizes specifically to the target molecule. A secondary probe, referred to herein as a bridging molecule, binds to the primary probe and hybridizes to a tertiary probe, referred to herein as a developer molecule. The developer molecules may be self-complementary.

The relationship of the probes to each other are important. The formula for the three types of linear probes may be represented as follows:

Primary probe:

I

II

Bridging molecule:

$$Y_i\text{—}Z_z\text{—}C_c \qquad \text{III}$$

$$_zZ\text{—}B'_b\text{—}Z_z\text{—}C_c\text{—}Z_z \qquad \text{IV}$$

Developer Molecule:

$$Z_z\text{—}C'_c\text{—}Z_z\text{—}C''_c\text{—}Z_z \qquad \text{V}$$

In the Formulae above, "Z" represents a nucleotide sequence that may or may not be present. Each nucleotide sequence represented by "Z" is independent of all the other nucleotide sequences represented by "Z". "z" may represent 0–100. Preferably, "z" represents 0.

Referring now to the drawings, the primary probe (15) may be represented by Formula I. "A" represents the first sequence of the primary oligonucleotide probe (10). The sequence represented by "A" contains a nucleotide sequence that is complementary to a sequence of the target molecule (2). The number of nucleotides in the sequence is represented by "a". "a" represents an integer between 6–100, preferably between 8–30, and more preferably between 10–26.

"X" represents a group that is part of the means for binding the primary probe to the bridging molecule (20). "X" may, for example, represent a ligand capable of binding to a receptor ("Y") on bridging molecule (20). Preferably, however, "X" represents a second sequence of the primary probe that is complementary to a sequence of the bridging molecule. This second sequence of the primary probe is shown as (50) in FIG. 2, and as "B" in Formula II. The number of nucleotides in sequence "B" is represented by "b". "b" represents an integer between 6–100, preferably between 8–26, and more preferably between 12–24.

The bridging molecule (20) may be represented by Formula III. "Y" in Formula III represents part of the means for binding the primary probe to the bridging molecule. "Y" may, for example, be a receptor for ligand "X" of the primary probe. Preferably, however, "Y" represents a sequence of nucleotides, "B'", that is capable of hybridizing to the second sequence of the primary probe (50), which is represented by "B" in Formula II. The number of nucleotides in sequence "B'" is represented by "b", which has been defined above.

"C" in Formula III and IV represents a nucleotide sequence that hybridizes to a sequence in a developer molecule (40). The number of nucleotides in sequence "C" is represented by "c". "c" represents an integer that has the same definitions as "b" defined above.

The developer molecule (40) is shown in Formula V. "C'" represents the sequence in the developer molecule that hybridizes to sequence "C" in Formulae III and IV. The number of nucleotides in sequence "C'" is represented by "c", which has been defined above. "C''" is a sequence in the developer molecule that is complementary to at least one sequence in at least one other developer molecule, and may be complementary to sequence "C'". The number of nucleotides in "C''" is "c", which has been defined above. "C" and "C''" may represent the same or different sequences. Preferably, "C" and "C''" represent the same sequence. When "C" and "C''" do not represent the same sequence, they each hybridize to a different sequence of the developer molecule. Both of these sequences are represented by "C'", even though they are not necessarily the same sequence.

It is advantageous for "B" and "B'", "C" and "C'", and "C'" and "C''" to hybridize selectively to each other. Therefore, none of these sequences should be complementary to a sequence of the target molecule containing a significant number of nucleotides.

Self Complementary Developer Molecules

In one embodiment of the invention, the developer molecules are self-complementary. Important advantages occur when the sequence of the branches of the developer molecule are chosen carefully. The sequences of the developer molecules that hybridize to each other, C' and C'' in Formula V, should hybridize uniquely so that it is possible to predict how many nucleotides in a hybridized developer molecule participate in hybridization. As mentioned above, it is preferable for all of the nucleotides of the developer molecule to be hybridized.

In addition, it is preferable for the hybridizing sequence of each branch to contain at least two of the four possible different nucleotides, preferably at least three different nucleotides and more preferably all four possible nucleotides (or hybridizable analogs thereof). Preferably, each of the four nucleotides or analogs thereof constitute at least 5%, preferably at least 10%, and more preferably at least 15% of the total number of nucleotides in a complementary sequence (i.e., A, B, B', C, C', and C'' in Formula I–V).

It is advantageous to minimize the number of different developer molecules required for an assay. In order to achieve this minimum number of developer molecules, it is preferable for each branch of each developer molecule to hybridize to many branches of other developer molecules. Most preferably, every branch of every developer molecule hybridizes to every branch of every other developer molecule. This result is achieved by providing a branch having a nucleotide sequence with two portions. Each portion is the inverted complement of the other portion. If the sequence were double-stranded, the two portions would be palindromic. An example of a suitable inverted complementary sequence is shown in Formula VI:

$$(Z_z)\text{CCAAG}(Z_z)\text{CTTGG}(Z_z) \qquad \text{(VI)}$$

wherein Z and z are as defined above. Any such inverted, complementary sequence is suitable.

An advantage of an inverted, complementary sequence such as that exemplified in Formula VI above is that it is uniquely self-complementary. The nucleotides involved in hybridization are known precisely.

If a developer molecule consists of branches comprising an inverted complementary sequence, each branch will hybridize to a branch of another developer molecule having the same sequence as itself under suitable conditions. Such developer molecules are referred to herein as self-complementary developer molecules. Each such developer molecule can have the same structure as all the other developer molecules, minimizing thereby the number of branches and developer molecules that must be prepared.

Each branch comprising an inverted complementary sequence in a developer molecule may be the same or different. There may be as many different sequences as there are branches in a developer molecule, as long as each branch comprises a sequence that is an inverted complement. It is also possible for some of such branches to be the same and some to be different. To minimize both the number of oligonucleotides that must be prepared and the time required for hybridization, it is preferred for each developer molecule to consist of identical branches. An example of a developer molecule having two different inverted complementary branches is shown as Formula VI':

CGCATGCGATGATCAT　　　　　　　　　　VI'

It is desirable to prevent complementary branches in the same developer molecule from hybridizing to each other. This result can be achieved by preparing molecules having the proper symmetry. For example, a developer molecule having two branches, each of which comprising the inverted, complementary sequence shown above as Formula VI when z represents 0, may have the structure shown in either Formula VI A or VI B:

CCAAGCTTGGCCAAGCTTGG　　　　　　　VI A

CCAAGCTTGGGGTTCGAACC　　　　　　　VI B

In Formula VI A, the ten nucleotides that constitute one branch of the molecule can fold back and hybridize to the ten nucleotides of the other branch. Such internal hybridization of branches is undesirable.

Internal hybridization of branches is not possible in the structure of Formula VI B. Therefore, the structure of Formula VIB is preferred.

It is possible to predict which of the two possible structures of a linear oligonucleotide having two branches, each of which comprises an inverted complementary sequence, will not lead to internal hybridization of the branches. The molecule that avoids the internal hybridization is capable of assuming a conformation that has a two-fold axis of symmetry, i.e., $C_2$ symmetry. For example, Formula VI B has $C_2$ symmetry.

In general, it is preferable that the developer molecule have $C_n$ symmetry, wherein "n" represents the number of branches. When the developer molecule is branched, n is at least 3. In developer molecules having Cn symmetry, each branch is capable of hybridizing to every branch of other developer molecules, but is incapable of hybridizing to the branches of the same developer molecule.

In addition to the nucleotides shown in Formula VI A and VI B, each branch may have additional nucleotides, as shown by $Z_z$ in Formula VI when z does not represent 0. The presence of such additional nucleotides would destroy the formal $C_n$ symmetry. What is important is that the symmetry relationship be retained for that part of each branch that constitutes the inverted, complementary sequence. The nucleotide sequences represented by Z may be ignored for determining the preferred symmetry of the developer molecule.

Although the branches in a developer molecule having inverted, complementary sequences and $C_n$ symmetry as defined above cannot hybridize to other branches in the same developer molecule, each half of the inverted, complementary sequence can hybridize to the other half, either in the same branch or in another branch of the same molecule. An example of a branch in a three-branched developer molecule hybridizing to itself is shown in Formula VII:

CCAAG(Z)$_z$CTTGG————GGTTC(Z)$_z$GAACC

The problem of internal hybridization may be avoided by taking advantage of the fact that the undesirable intra-branch hybridization involves half the number of nucleotides as the desired hybridization between two branches from different developer molecules. In the example shown in Formula VII, the undesirable hybridization of a branch within a developer molecule involves five nucleotides. The desirable hybridization between two branches from different developer molecules would involve ten nucleotides. Therefore, the stringency of the hybridization conditions is selected so that five nucleotides will not stably hybridize, while ten nucleotides will stably hybridize. The desired stringency be determined by those having ordinary skill in the art. For example, at temperatures between 22 and 30 degrees centigrade, five nucleotides will not stably hybridize, but ten nucleotides will stably hybridize.

It should be understood that two nucleotide sequences are considered to hybridize to each other or to be complementary to each other if they are sufficiently complementary to each other to hybridize under normal conditions. Normal conditions of hybridization have been described above. Preferably, the nucleotide sequences that hybridize to each other (i.e, A and a sequence of the target molecule, B and B', C and C', and C' and C") are perfectly complementary. There may, however, be exceptions to complementarity in hybridizing sequences, as is well known. The longer the hybridizing sequences, the more exceptions may occur without forfeiting the ability to hybridize under normal conditions.

Moreover, although ranges of values for the number of complementary nucleotides in hybridizing sequences, i.e. a, b, and c, in Formula I-V, have been given, these ranges are not critical. The minimum number of nucleotides in a complementary sequence is the number that stably hybridizes under normal hybridizing conditions as described above. The stringency of the conditions generally increases as the number of complementary nucleotides increases. The minimum number of complementary sequences is typically 6, preferably 12, and more preferably 16.

There is no necessary upper limit to the number of complementary nucleotides capable of hybridizing to each other. The upper limit is, rather, governed by practical considerations, such as cost and time required for hybridization. Therefore, in the present invention, the maximum number of nucleotides in a sequence that hybridizes to another sequence typically does not exceed 100, preferably 40, and more preferably 24.

It is possible to design a developer molecule having a sequence that hybridizes to the target nucleic acid molecule. In such a case, the first developer molecule, which hybridizes to the target nucleic acid molecule, is considered the primary probe, and the second developer molecule or molecules, which hybridize to the primary probe, is considered to be the bridging molecule.

In order to maximize the efficiency of the presently described method and the stability of the complex of nucleic acid molecules formed, it is preferable for all of the nucleotides of the bridging molecule to hybridize either to the second segment of the primary probe or to at least one developer molecule, so that there are no unhybridized nucleotides in the hybridized bridging molecule. Moreover, it is further preferred for 30%–70%, preferably 40%–60%, and more preferably 45%–55% of the nucleotides of a linear bridging molecule to hybridize to the primary probe and the remaining 70%–30%, preferably 60%–40%, and more preferably 55%–45% of the nucleotides of the bridging molecule to hybridize to at least one developer molecule.

Similarly, it is preferable for all of the nucleotides of the developer molecule to hybridize to the bridging molecule and at least one other developer molecule, or to at least two other developer molecules in the developer chain, except for the last developer molecule in the developer chain, which may hybridize to as few as one other developer molecule, so that all of the nucleotides of the developer molecule are hybridized. Further, it is preferable for 30%–70%, preferably 40%–60%, and more preferably 45%–55% of the nucleotides of each linear developer molecule in the developer chain to hybridize to the bridging molecule or to at least one additional developer molecule, and the remaining 70%–30%, preferably 60%–40%, and more preferably 55%–45% of the nucleotides of each developer molecule, except for the last developer molecule in the chain, to hybridize to at least one additional developer molecule.

Figure 3:
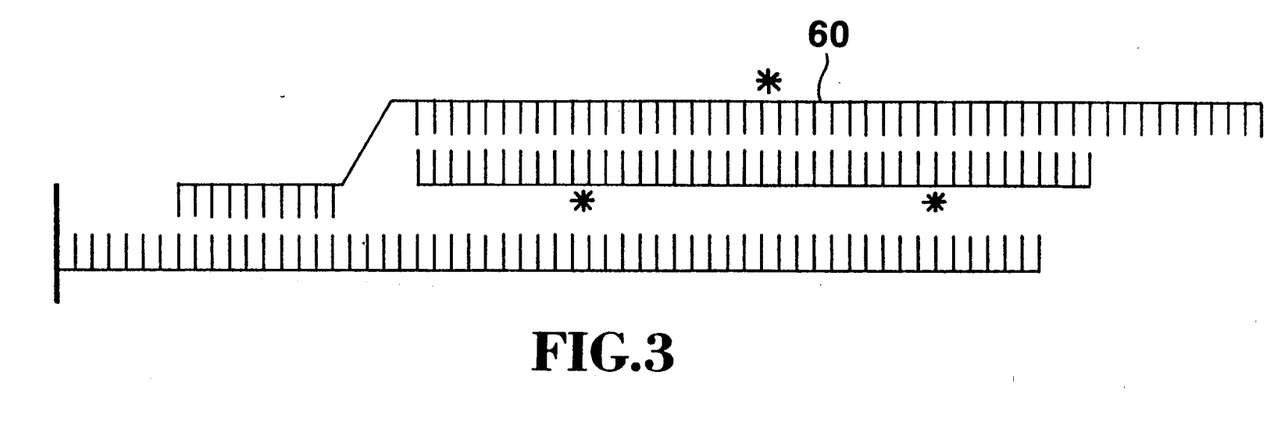

When all of the nucleotides of the bridging molecule (20) hybridize either to all of the nucleotides of the second segment (50) of the primary probe (15) or to all of the nucleotides of at least one developer molecule (40), there will be no nucleotides of the bridging molecule that are not hybridized. Under such circumstances, one end of the second sequence of the primary probe (50) will be adjacent to an end of a first developer molecule (52) with no gap between them, as shown in FIG. 2. The end of the second segment of the primary probe may be ligated to the adjacent end of the developer molecule, as shown in FIG. 3.

When all of the nucleotides of each developer molecule hybridize either to the bridging molecule and at least one other developer molecule, or to at least two other developer molecules in the developer chain, except for the last developer molecule in the developer chain, which may hybridize to as few as one other developer molecule, there will be no gaps between the bridging molecule (20) and an end of the second developer molecule (54) in the developer chain or between the ends of the developer molecules in the developer chain. Thus, an end of the first developer molecule (52) will be adjacent to an end of the third developer molecule (56), as shown in FIG. 2. The other end of the third developer molecule will be adjacent to an end of the fifth developer molecule, and so on. Similarly, an end of the second developer molecule will be adjacent to an end of the fourth developer molecule. The other end of the fourth developer molecule will be adjacent to an end of the sixth developer molecule. Under such conditions, the adjacent ends of the bridging molecule and the developer molecules may all be ligated to each other.

In view of the above, it is possible to ligate the primary probe, the bridging molecule and the developer molecules in the developer chain together to form a concatamer. Such a concatamer is shown as (60) in FIG. 3. The number of developer molecule units in the concatamer may be as large as 100, 1,000, 10,000, and even more. In view of the label on each developer molecule, the amplification of the signal is significant.

For maximum stability, one strand of ligated developer chain is ligated to the primary probe and the other strand of ligated developer chain is ligated to the bridging molecule. Such a structure is shown in FIG. 3. In addition, if the target nucleic acid molecule is linear and if the sequence of the target nucleic acid molecule that hybridizes to the primary probe occurs at an end of the target nucleic acid molecule, the target nucleic acid molecule may be hybridized to the bridging molecule.

The ligations described above may be accomplished with a suitable enzyme. Some suitable enzymes include, for example, ligase.

Branched Probes and Molecules

The primary probe, bridging molecule and developer molecule may be linear or branched. A molecule is considered to be linear for the purposes of this specification if it has two branches and to be branched if it has three or more branches. Each branch comprises a sequence that is capable of hybridizing to a sequence in a branch of the target molecule or of a primary probe, bridging molecule or developer molecule. The branches of branched probes and molecules in accordance with the invention need not be different from the branches of linear probes and molecules.

Linear oligonucleotides as well as the individual branches of branched oligonucleotides may be synthesized by methods known in the art. For example, the automated phosphoramidite method of Warner et al, *DNA* 3, 401 (1984) may be used.

Branched molecules containing DNA sequences may suitably be prepared by methods known in the art. For example, branched molecules may be prepared by joining the branches through a linker group. The linker group may comprise a multifunctional molecule that is capable of binding to oligonucleotides, preferably to the 5' or 3' end of the oligonucleotides. Suitable multifunctional groups are described in Segev, European patent application 292,128. The linker group may also be a group attached to one or more of the nucleotides in the oligonucleotide.

Figure 4:
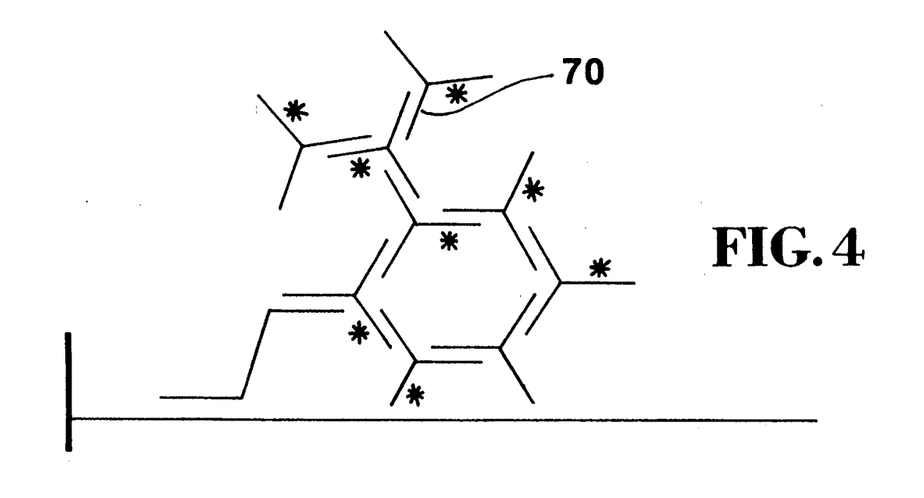

Branched nucleic acid molecules for use in the present invention may be prepared in accordance with Urdea et al, EP 317,077. For example, the Urdea et al application discloses comb structures in FIG. 3-1 and at page 8, line 38 et seq; fork structures in FIG. 3-2 and at page 10, line 7 et seq; multiple fork and forked comb structures in FIGS. 3-3 and 3-4, respectively, and at page 10, line 26 et seq; and multiple comb structures in FIG. 3-5, and at page 10, line 30 et seq. The synthesis of such branched structures is described in Example 2B.

When a developer molecule is branched, each branch should be capable of hybridizing to at least one branch of another developer molecule. Preferably, no branch of a developer molecule is capable of hybridizing internally to another branch of the same molecule.

For example, a developer molecule having three branches, each of which comprises the inverted, complementary sequence shown above as Formula VI, may have the structure shown in Formula VIII:

wherein ¹³ — represents a linking group. In Formula VIII, there is a three-fold axis of symmetry, i.e., $C_3$ symmetry. Therefore, none of the branches can internally hybridize to another branch in the same molecule.

The bridging molecule may also be branched. One branch (B′ in Formula II) of the bridging molecule hybridizes to the second sequence of the primary probe (B in Formula I). The remaining branches preferably comprise inverted, complementary sequences identical to those used in the developer molecules. More preferably, the second sequence of the primary probe comprises the same inverted, complementary sequence as occurs in each branch of the developer molecule. In such as case, the bridging molecule will be identical to the developer molecule, further minimizing the number of different molecules required to be prepared for the assays of the present invention.

The primary probe may also be branched. The first sequence of the primary probe is complementary to a sequence of the target molecule. The second sequence of the primary probe, which hybridizes to the bridging molecule, may appear on multiple branches.

The total number of branches in the primary probe, the bridging molecule and the developer molecule is at least two. Preferably, there are three or more branches. The upper limit of the number of branches is that necessary to prevent excessive steric hindrance. Normally, there will not be more than 5 branches, preferably not more than 3 branches.

Preferably, there are 3–5 branches in the developer molecules, and/or the bridging molecules, and/or the primary probe. It is most important for the developer molecule to be branched, since there are more developer molecules than bridging molecules or primary probes. The presence of branched developer molecules leads to exponential signal amplification of $(Q-1)^r$, wherein "Q" represents the number of self-complementary branches and "r" represents the number of developer molecules in a chain following hybridization.

Pairs of Non-self-hybridizable Developer Molecules

Instead of self-complementary branched developer molecules, it is possible to use a pair of linear or branched developer molecules. Each member of the pair has a different structure that is not self-complementary. Each branch of one member of such a pair hybridizes to at least one branch of the other member of the pair. Preferably, the sequence of each branch in each member of the pair is identical. So that each branch of one member of the pair hybridizes to each branch of the other member of the pair.

It is also preferable for the branches of such branched developer molecules to hybridize uniquely to its complementary partner. Unique hybridization for the purposes of this specification means that when a sequence hybridizes to its complementary partner, the same number of nucleotides hybridizes each time. For example, a branch consisting of homopolymeric oligonucleotides, i.e. poly-A, can hybridize to its complementary partner, i.e. poly-T, in almost as many ways as there are nucleotides in the oligonucleotide. Such unpredictability is disadvantageous. Preferably, therefore, the sequence of each branch contains at least two different nucleotides, preferably at least three different nucleotides, and more preferably all four nucleotides.

In order to avoid the hybridization of half of each such sequence to the other half, it is preferable if the branches contain no sequences that constitute inverted complements. Except as indicated above, the branches of the pair of non-self-complementary developer molecules are similar to the branches of the self-complementary developer molecules described earlier, and may be prepared the same way.

An example of a pair of non-self-complementary developer molecules useful in this embodiment of the invention is illustrated in Formula IX and X:

Assays

The present invention is useful in a large variety of known hybridization procedures. An assay, according to the present invention, involves at least the following steps:

i) hybridizing a target nucleic acid molecule to a first sequence of a primary probe;

ii) binding the primary probe to a bridging molecule, preferably through a second sequence of the primary probe that is complementary to a nucleotide sequence on the bridging molecule;

iii) hybridizing the bridging molecule to at least one labelled developer molecule;

iv) hybridizing at least one additional labelled developer molecule, forming thereby a chain of labelled developer molecules; and v) detecting the labelled developer molecules.

The assay may, for example, occur in a liquid phase. Preferably, the target nucleic acid molecule is immobilized on a solid surface. Immobilization may occur by covalently attaching the target nucleic acid molecule to the solid support, as described, for example, by Albarella et al, EP 144,914; Dattagupta et al, EP 130,523; or Yabusalu et al, WO 85/02628. The target nucleic acid molecule may also be immobilized on the solid support by non-covalent means. for example, the target nucleic acid molecule may be bound to the solid support by means of a ligand-receptor interaction. A sandwich hybridization method wherein the target nucleic acid molecule hybridizes to an immobilized nucleotide sequence in a way that does not interfere with hybridizing the target to the primary probe is also possible.

Immobilizing the target nucleic acid molecule may occur before hybridizing the primary probe to the target nucleic acid molecule. Alternatively, the target nucleic acid molecule may be immobilized after binding the target nucleic acid molecule to the primary probe, to the bridging molecule or to the developer molecules. The immobilization step may also occur simultaneously with any of these steps. The advantage of immobilizing the target nucleic acid molecule is that the unhybridized labelled molecules may be separated from the immobilized complex prior to detection, thereby reducing the background and increasing the signal-noise ratio.

I claim:

1. A method for detecting target nucleic acid molecules comprising the steps of:
   a) hybridizing a first sequence of a primary oligonucleotide probe to the target nucleic acid molecules wherein the probe has a means for binding to a bridging oligonucleotide, the bridging oligonucleotide being capable of hybridizing to at least one self-complementary developer oligonucleotide;
   b) exposing the probe to the bridging oligonucleotide and to a plurality of self-complementary developer oligonucleotides having at least three branches, each branch of the developer oligonucleotide having a sequence of at least six nucleotides; each developer oligonucleotide:
      i) having the same structure as all other developer oligonucleotides; and
      ii) optionally containing, a detectable label;
   under conditions such that:
      i) the bridging oligonucleotide binds to the primary probe and hybridizes to at least one developer oligonucleotide, and
      ii) at least two additional developer oligonucleotides hybridize to the first developer oligonucleotide; and
      iii) a plurality of other developer oligonucleotides hybridize to the hybridized additional developer oligonucleotide to form a branched developer oligonucleotide chain; and
   c) detecting the branched developer oligonucleotide chain, thereby detecting the target nucleic acid molecules.

2. The method of claim 1 wherein each branch of the developer oligonucleotide comprises a sequence of at least six nucleotides that is identical in one direction and complementary in the opposite direction to the sequence of nucleotides in every other branch.

3. The method of claim 2 wherein the sequence consists of an inverted, complementary sequence.

4. The method of claim 1 wherein the developer oligonucleotide exhibit $C_n$ symmetry if nucleotides not part of the inverted, complementary sequence are ignored, wherein C represents the developer oligonucleotide branches and "n" represents the number of branches.

5. The method of claim 1 wherein the bridging oligonucleotide is branched.

6. The method of claim 1 wherein the bridging oligonucleotide and the developer oligonucleotides are identical.

7. The method of claim 1 wherein the primary probe is branched.

* * * * *